US011547286B2

(12) United States Patent
Sellers (10) Patent No.: US 11,547,286 B2
(45) Date of Patent: Jan. 10, 2023

(54) STYLET ASSEMBLY

(71) Applicant: Brio13Inv. LLC, Waukesha, WI (US)

(72) Inventor: Mark G. Sellers, Nashotah, WI (US)

(73) Assignee: BRIO13INV. LLC, Waukesha, WI (US)

( * ) Notice: Subject to any disclaimer, the term of this patent is extended or adjusted under 35 U.S.C. 154(b) by 207 days.

(21) Appl. No.: 16/749,559

(22) Filed: Jan. 22, 2020

(65) Prior Publication Data
US 2021/0219819 A1  Jul. 22, 2021

(51) Int. Cl.
| A61B 1/005 | (2006.01) |
| A61B 1/045 | (2006.01) |
| A61B 1/00 | (2006.01) |
| A61B 1/01 | (2006.01) |
| A61B 1/06 | (2006.01) |
| A61B 1/313 | (2006.01) |
| A61M 25/01 | (2006.01) |

(52) U.S. Cl.
CPC ........ *A61B 1/0052* (2013.01); *A61B 1/00009* (2013.01); *A61B 1/0011* (2013.01); *A61B 1/00078* (2013.01); *A61B 1/01* (2013.01); *A61B 1/045* (2013.01); *A61B 1/06* (2013.01); *A61B 1/00052* (2013.01); *A61B 1/313* (2013.01); *A61M 25/0102* (2013.01)

(58) Field of Classification Search
CPC .............. A61B 1/0051; A61B 16/0418; A61B 16/0488; A61B 25/0102; A61B 25/0133; A61B 2025/0161; A61B 1/06; A61B 1/01; A61B 1/0011; A61B 1/00078; A61B 1/045
See application file for complete search history.

(56) References Cited

U.S. PATENT DOCUMENTS

| 4,078,555 A | * | 3/1978 | Takahashi | A61B 1/0052 188/72.1 |
| 4,360,008 A | * | 11/1982 | Corazzelli, Jr. | A61B 1/267 600/120 |
| 4,436,087 A | * | 3/1984 | Ouchi | A61B 1/00089 600/106 |
| 5,114,402 A | * | 5/1992 | McCoy | A61B 1/0051 600/143 |
| 5,423,814 A | * | 6/1995 | Zhu | A61B 17/0218 606/41 |

(Continued)

OTHER PUBLICATIONS

PCT International Search Report for PCT/US2021/014137, dated May 12, 2021.

*Primary Examiner* — John P Leubecker
*Assistant Examiner* — Jae Woo
(74) *Attorney, Agent, or Firm* — Boyle Fredrickson S.C.

(57) ABSTRACT

A stylet assembly and method of forming an in vivo image acquiring stylet assembly. The stylet assembly includes an elongate flexible body and an image acquiring device that is supported at a location that is offset from an in vivo facing terminal end of the stylet assembly. A terminal end portion of the stylet assembly is defined by a manipulator that is oriented to extend in a crossing direction relative to a longitudinal axis of the elongate body. The terminal end portion of the stylet assembly is steerable relative to the elongate body and is operable to manipulate positions or adjacent anatomy and/or effectuate guidance of the imaging device relative thereto during use.

16 Claims, 4 Drawing Sheets

(56) References Cited

U.S. PATENT DOCUMENTS

| | | | | |
|---|---|---|---|---|
| 5,562,619 | A * | 10/1996 | Mirarchi | A61B 17/221 604/264 |
| 5,836,894 | A * | 11/1998 | Sarvazyan | A61B 8/0825 600/587 |
| 5,876,325 | A * | 3/1999 | Mizuno | A61B 1/00188 600/102 |
| 5,922,018 | A * | 7/1999 | Sarvazyan | A61B 8/0825 600/587 |
| 5,993,466 | A * | 11/1999 | Yoon | A61B 17/062 606/144 |
| 5,993,467 | A * | 11/1999 | Yoon | A61B 17/0469 606/147 |
| 6,929,600 | B2 | 8/2005 | Hill | |
| 9,901,714 | B2 * | 2/2018 | Lemon | A61M 25/09 |
| 10,173,317 | B2 * | 1/2019 | Sato | A61B 34/70 |
| 10,974,005 | B1 * | 4/2021 | Sun | A61M 16/0418 |
| 2002/0193741 | A1 * | 12/2002 | Secrest | A61B 17/3478 604/164.06 |
| 2003/0055442 | A1 * | 3/2003 | Laufer | A61B 17/0057 606/153 |
| 2004/0044350 | A1 * | 3/2004 | Martin | A61B 1/0057 606/139 |
| 2004/0158125 | A1 * | 8/2004 | Aznoian | A61B 17/0482 600/106 |
| 2004/0220451 | A1 * | 11/2004 | Gravenstein | A61B 1/00165 600/139 |
| 2006/0069303 | A1 * | 3/2006 | Couvillon, Jr. | A61B 1/00087 600/104 |
| 2007/0265499 | A1 * | 11/2007 | Wood | A61B 1/00091 600/137 |
| 2007/0270661 | A1 * | 11/2007 | Philippon | A61B 18/148 600/300 |
| 2008/0058605 | A1 * | 3/2008 | Sorensen | A61B 1/32 600/208 |
| 2008/0108869 | A1 * | 5/2008 | Sanders | A61B 1/00103 600/109 |
| 2008/0236575 | A1 * | 10/2008 | Chuda | A61B 1/05 128/200.26 |
| 2008/0275483 | A1 * | 11/2008 | Makower | A61B 17/0218 606/192 |
| 2009/0171161 | A1 * | 7/2009 | Ewers | A61B 1/0052 600/149 |
| 2009/0216077 | A1 * | 8/2009 | Banju | A61B 1/018 600/103 |
| 2010/0049225 | A1 * | 2/2010 | To | A61B 17/320758 606/159 |
| 2010/0210923 | A1 * | 8/2010 | Li | A61N 1/056 600/301 |
| 2011/0112434 | A1 * | 5/2011 | Ghabrial | A61B 17/3423 600/564 |
| 2011/0160537 | A1 | 6/2011 | Chen | |
| 2011/0295242 | A1 * | 12/2011 | Spivey | A61B 17/320016 606/1 |
| 2012/0157765 | A1 * | 6/2012 | Mitelberg | A61B 1/018 600/106 |
| 2012/0302833 | A1 * | 11/2012 | Hayman | A61M 16/0486 600/120 |
| 2013/0024024 | A1 * | 1/2013 | Namiki | A61B 1/00149 700/245 |
| 2013/0331646 | A1 * | 12/2013 | Pell | A61B 1/3132 600/106 |
| 2014/0123976 | A1 * | 5/2014 | Mccormick | A61M 16/0488 128/200.26 |
| 2014/0275772 | A1 | 9/2014 | Chuda | |
| 2015/0327750 | A1 * | 11/2015 | Ogawa | A61B 1/2733 600/106 |
| 2016/0135913 | A1 * | 5/2016 | Kishi | A61B 1/0055 606/130 |
| 2016/0345807 | A1 * | 12/2016 | Yoshimura | G02B 23/2476 |
| 2016/0374772 | A1 * | 12/2016 | Hasegawa | A61B 34/37 606/130 |
| 2017/0209022 | A1 * | 7/2017 | Molnar | A61M 16/0461 |
| 2017/0231475 | A1 | 8/2017 | McWeeney et al. | |
| 2018/0250484 | A1 * | 9/2018 | McCormick | A61B 1/00039 |
| 2019/0059710 | A1 * | 2/2019 | Molnar | A61M 16/0434 |
| 2019/0217034 | A1 * | 7/2019 | Maslow | A61B 1/0125 |
| 2020/0060718 | A1 * | 2/2020 | Patel | A61B 5/6852 |
| 2020/0178787 | A1 * | 6/2020 | Gerrans | A61B 1/0056 |
| 2020/0205909 | A1 * | 7/2020 | Penny | A61B 1/00149 |
| 2020/0297957 | A1 * | 9/2020 | Poormand | A61M 16/0672 |
| 2020/0367722 | A1 * | 11/2020 | Perez-Lizano | A61B 1/0676 |
| 2020/0405990 | A1 * | 12/2020 | Blom | A61M 16/0488 |

* cited by examiner

STYLET ASSEMBLY

BACKGROUND OF THE INVENTION

The present application relates generally to in vivo imaging, and more particularly, to an assembly and method of providing an imaging stylet assembly having an in vivo end whose shape or configuration can be manipulated when located within a subject to manipulate adjacent anatomy and to guide the imaging acquiring device toward areas of the anatomy desired to be inspected.

During various medical procedures, it is occasionally desirable or even necessary to visually inspect areas, anatomy, or passageways of a subject that are not ordinarily readily available or sufficiently accessible to accommodate visual inspection from anatomical openings, in vitro locations or locations elsewhere outside of an organism, living or deceased, and/or with the aid of generally non-intrusive medical diagnostic tools such as otoscopes, ophthalmoscopes, bronchoscopes, imaging laryngoscopes, or the like. To aid in such inspection and diagnosis, stylets are commonly employed to facilitate the visual inspection, whether via optical eyepiece or electronic image acquiring devices such as cameras or the like, and/or manipulation of internal anatomy and/or placement of medicinals and/or ancillary devices wherein such inspection, treatment, and/or manipulation is not readily available or accessible by less intrusive methodologies or methodologies that are otherwise external to or in vitro to the subject. Although any anatomic or surgically created openings are suitable for interaction with such devices, many consider the in vivo introduction of such appliances via the respiration passage of the subject and associated with endotracheal intubation to be the least intrusive methodology where the anatomy associated with the desired inspection is accessible therethrough.

During endotracheal intubation procedures, a rigid laryngoscope is commonly inserted through the mouth of a subject and an intubation tube is passed via the mouth or nasal passages through the pharynx, past the tongue and epiglottis, through the vocal cords, and into the trachea. The endotracheal intubation device is commonly removed upon the desired placement of the intubation tube and/or other tube whose placement is guided via cooperation with intubation device. This tube is then used to maintain the airway and support ventilation of the lungs, a critical life support function. Using a straight or curved blade with a light along its length, the tongue and epiglottis are lifted out of the way allowing direct visualization of the vocal cords such that an endotracheal tube can be advanced into the trachea.

Periodically, various anatomical features or patient specific anatomy, which is commonly dynamic or ever changing in nature rather that static, can detrimentally affect visual inspection of, or interaction with, anatomy associated with the desired placement of the endotracheal tube and/or interaction and/or visual inspective at locations that are further in vivo of the subject larynx opening. Video or imaging stylets are frequently employed to facilitate inspection, manipulation, treatment, sectioning, and/or other interactions with anatomy that is positioned further in vivo than the larynx opening when inspection via the oral opening is employed. It is appreciated that such application is one of many uses associated with application of imaging or other stylet configurations.

Although helpful for in vivo inspection and manipulation of anatomy, whether oral, anal, or surgical application, available imaging stylets suffer from various drawbacks. Commonly, such devices include an image acquiring device that is disposed at the distal in vivo directed end of the appliance. Many such devices are flexible along the longitudinal length of the stylet assembly and still others are equipped with adjustment mechanisms that can be employed to manipulate the relative elongate configuration of the assembly. Rotation and/or operation of an operator relative to the patient can be employed to manipulate the relative position, configuration, or orientation of the in vivo end of the stylet assembly relative to anatomy proximate thereto to facilitate the desired positioning of the imaging device.

Unfortunately, the proximity of the image capturing device relative to the in vivo distal end of the assembly frustrates the ability of a user to manipulate subject anatomy or the configuration of the stylet assembly in a manner that accommodates both visual inspection of obstructing structures or anatomy and manipulation of the relative position and/or configuration of the stylet assembly relative thereto. That is, commonly, the only remediation available to use of such assemblies and to further the introduction of the assembly along an intended or desired path, depth, or position relative to the patient is to manipulate the relative rotational orientation of the assembly and/or interact the control arrangement to manipulate the presentation angle associated with the terminal end of the assembly and reattempt the progression of the introduction of the device beyond a respective obstruction. Visual inspection associated with the progressing interaction of the distal end of the assembly is commonly unavailable as the obstructing anatomy or structures obstruct the image capturing device as the same is introduced thereto. Such configurations require the user to repeatedly introduce and retract the stylet assembly until such time as the obstructing structures can be avoided and the in vivo end of the stylet assembly is allowed to pass thereby.

Still further, in applications where anatomy or obstructing structures are disposed in close or overlapping orientations relative to a desired area of inspection, the ability of the user to inspect areas of interest located closely therebehind can be rendered difficult if even possible with known stylet assemblies. That is, instances of close proximity between areas of interest and obstructing structures can require the introduction of additional assemblies in parallel with the stylet assembly to facilitate translation of obstructing structures or anatomy such that areas of interest disposed therebehind can be inspected via exposure to the field of view associated with the image capturing device.

Accordingly, there is a need for an stylet assembly that can be economically produced and which is operable to facilitate visual inspection of in vivo anatomy and features from locations in vitro relative to the patient or subject and which is constructed to facilitate translation of obstructing structures and features and does so in a manner that accommodates visual inspection of the translation operation. In a preferred aspect, the stylet assembly is constructed to facilitate in vivo visual inspection of both the translation operation as well as a manipulator defined by the stylet assembly and constructed to accommodate the translation operation.

SUMMARY OF THE INVENTION

The present application discloses a visual stylet assembly and method of forming a stylet assembly that overcomes one or more of the shortcomings disclosed above.

One aspect of the present application discloses a stylet assembly and method of forming an in vivo image acquiring stylet assembly that includes an elongate flexible body and an image acquiring device that is supported at a location that is offset from a terminal end of the stylet. A terminal end portion of the stylet assembly is defined by a manipulator that is oriented to extend in a crossing direction relative to a longitudinal axis of the elongate body. The terminal end portion of the stylet assembly is steerable relative to the elongate body and is operable to manipulate positions or adjacent anatomy and/or effectuate guidance of the imaging device relative thereto during use.

Another aspect of the present application that is useable or combinable with one or more of the features, aspects, or objects disclosed above discloses a stylet assembly having a tube that defines a passage therethrough. An image acquisition device, such as a camera, lens, or the like, is disposed proximate a first end of the tube. A connector is formed at the first end of the tube and is constructed such that the camera is operable therethrough. A manipulator that is defined by a flexible body extends outward from the connector and is oriented to extend in a crossing direction relative to a longitudinal axis of the tube such that a distal end of the manipulator forms a distal end of the stylet assembly. The manipulator is offset in a longitudinal and radial direction from the camera and is offset from a longitudinal axis of the tube such that a distal end of the manipulator is disposed deeper or further in vivo than the image acquisition device such that operation of the manipulator is capable of visual inspection by the image acquisition device.

A further aspect of the present application that is useable or combinable with one or more of the features, aspects, or features of the above aspects discloses a video stylet assembly having an elongate shaft that is constructed to pass through an opening in vivo. A connector is disposed proximate an in vivo end of the elongate shaft and an image capturing device is disposed proximate the connector. A guide extends in a longitudinal manner from the connector in a crossing direction relative to a longitudinal axis defined by the elongate shaft. The guide is oriented relative to the connector and the image capturing device such that a distal end of the guide can achieve positions within a field of view of the image capturing device during movement thereof.

Yet another aspect of the present application that is useable or combinable with one or more of the various features, aspects, or features of the above aspects discloses a method of forming an imaging stylet that includes providing a flexible outer housing having a patient facing end that is configured to pass in an in vivo direction. A connector is formed at the patient facing end of the housing and is inseparable therefrom. The method further includes forming the connector to receive an image acquisition device such that the image acquisition device is disposed proximate the patient facing end of the flexible outer housing. A manipulator is formed that extends further in the in vivo direction than the connector and is formed to be deflectable relative to the connector such that a distal end of the manipulator is disposed further in vivo than the image acquisition device and is operable to manipulate the orientation of anatomy or features relative thereto and in a manner that is preferably within a field of view of the image acquisition device.

These and various other aspects, features, and advantages of the invention will become apparent to those skilled in the art from the following detailed description and accompanying drawings. It should be understood, however, that the detailed description and specific examples, while indicating preferred embodiments of the present invention, are given by way of illustration and not of limitation. Many changes and modifications may be made within the scope of the present invention without departing from the spirit thereof, and the invention includes all such modifications.

BRIEF DESCRIPTION OF THE DRAWINGS

A clear conception of the advantages and features constituting the present invention, and of the construction and operation of typical mechanisms provided with the present invention, will become more readily apparent by referring to the exemplary, and therefore non-limiting, embodiment illustrated in the drawings accompanying and forming a part of this specification, wherein like reference numerals designate the same elements in the several views, and in which.

Before explaining the invention in further detail below with respect to the preferred embodiment shown in the drawings, it is to be understood that the invention is not limited in its application to the details of construction and the arrangement of the components set forth in the forthcoming description or as illustrated in the drawings. The invention is capable of other embodiments or being practiced or carried out in various ways. Also, it is to be understood that the phraseology and terminology employed herein is for the purpose of description and should not be regarded as nor is it intended to be limiting.

DETAILED DESCRIPTION OF THE PREFERRED EMBODIMENTS

In describing the preferred embodiment of the invention as illustrated in the drawings, specific terminology will be resorted to for the sake of clarity. However, it is not intended that the invention be limited to the specific terms so selected and it is to be understood that each specific term includes all technical equivalents which operate in a similar manner to accomplish a similar purpose. The various features and advantageous details of the subject matter disclosed herein are explained more fully with reference to the non-limiting embodiments described in detail in the following description.

Figure 1:
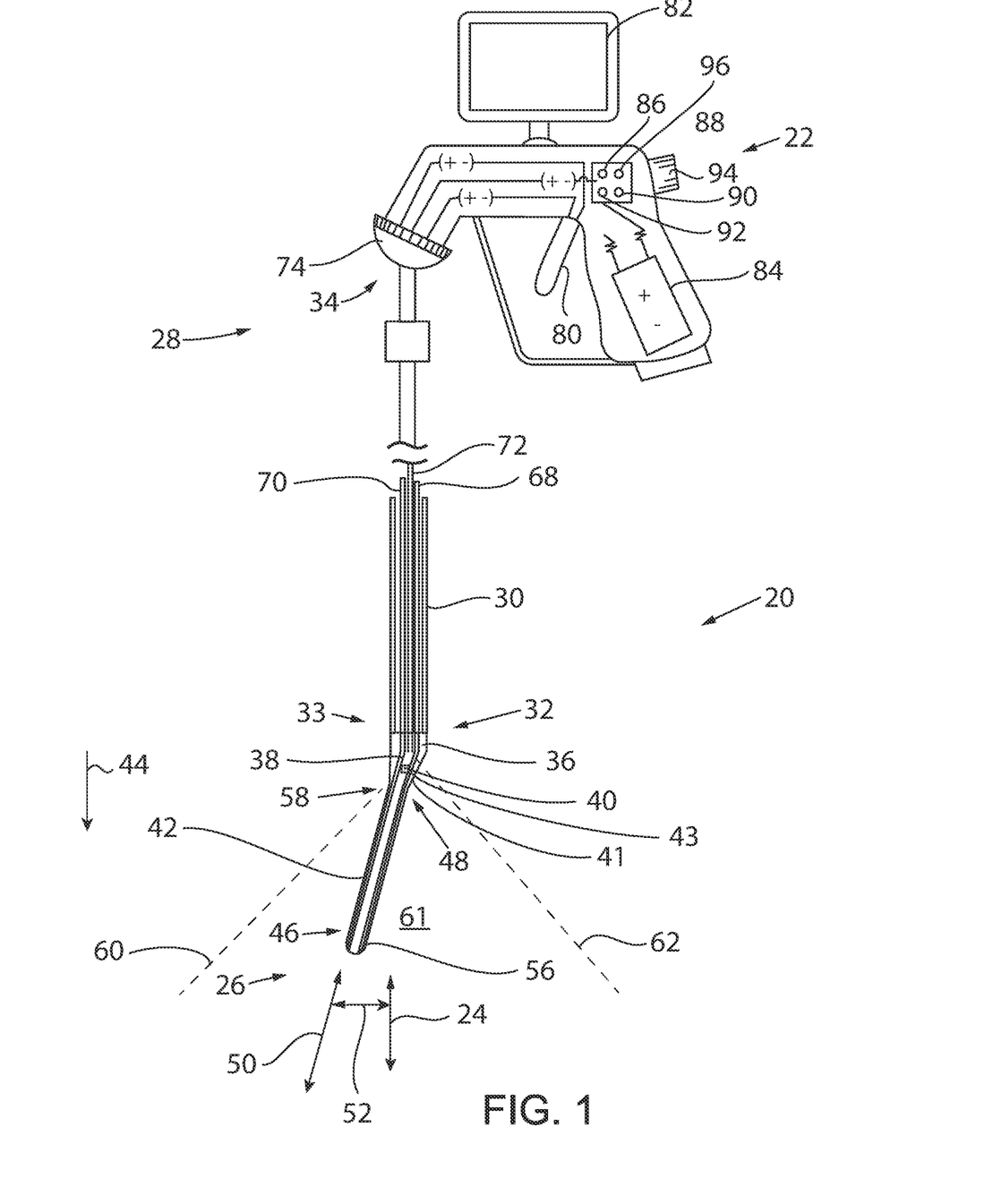
FIG. 1 is a side elevation graphical representation of an imaging stylet assembly according to the present invention.

FIG. 1 is a graphical representation of an in vivo video or imaging stylet assembly or simply stylet assembly 20 according to a preferred embodiment of the present invention. Stylet assembly 20 is preferably constructed to removeably cooperate with a controller or handle assembly 22 that remains outside the patient or subject undergoing penetration by stylet assembly 20 and is constructed to facilitate user interaction therewith. One such controller assembly is disclosed in U.S. Patent Application Publication No. 2008/0236575, the disclosure of which is incorporated herein. As disclosed further below, it is appreciated that stylet assembly 20 can be configured to cooperate with controller assemblies having construction and operational methodologies that are different than those disclosed in the '575 publication as such devices are commonly provided in various constructions and control methodologies intended to satisfy the demands and preferences of the user or operator during use of such devices to manipulate the relative configuration of stylet assembly 20 and/or the data or visual information garnered, inspected, and/or collected during use thereof.

Referring to FIG. 1, stylet assembly 20 extends in a generally longitudinal direction, indicated by line 24, between an in vivo, or direction toward a body of interest, facing end 26 and an in vitro, or direction outward or away from a body of interest, facing end 28 thereof. Stylet assembly 20 is defined by an elongate body or tube 30 that extends between the first end 32 and a second end 34. In the parlance used herein, first end 32 of tube 30 is nearer in vivo end 26 of stylet assembly 20 and second end 34 is nearer the in vitro or atmospheric directed end 28 of stylet assembly 20.

A connector 36 is secured, permanently affixed, or integrally formed with tube 30 and disposed at first end 32 thereof. Connector 36 defines a cavity 38, or is otherwise constructed to support, an image acquiring device 40—such as a camera, video camera or the like. A guide or manipulator 42 is secured, permanently affixed, or integrally formed with connector 36 such that manipulator 42 extends in an in vivo facing outward direction, indicated by arrow 44, relative to an in vivo or forward facing end 45 of connector 36. Manipulator 42 is defined by a body that extends between an in vivo facing or first end 46 and an in vitro or connector 36 facing second end 48.

When at rest or unacted upon in the manner disclosed further below, manipulator 42 extends in a longitudinal direction, indicated by arrow 50, that is preferably oriented at a crossing direction relative to the longitudinal axis 24 defined by tube 30. Although manipulator 42 is shown as being disposed at a relative angle, indicated by arrow 52, of approximately 15°, relative to axis 24 defined by tube 30, it is appreciated that angle 52 could be provided at other relative discrete angles between axes 24 and 50. Preferably, manipulator 42 extends in in vivo facing direction 44 at a crossing angle relative to the longitudinal axis 24 of stylet assembly 20. Preferably, angle 52 is less than 45 degrees and no less than approximately 5 degrees such that manipulator 42 preferably extends at an acute angle relative to the longitudinal axis 24 of stylet assembly 20 when at rest or otherwise unacted upon by adjacent anatomy and/or an elongate operator as disclosed further below.

Although tube 30 and manipulator 42 are disclosed above as being elongate tubular bodies that extend along respective longitudinal directions, as disclosed further below, both tube 30 and manipulator 42 are formed of non-rigid bodies such that the same are sufficiently deflectable of flexible to accommodate guided insertion and passage of the same to locations that are in vivo or internal to subjects via anatomical and/or surgical openings and the passages afforded by the adjacent anatomy associated therewith as disclosed further below. As disclosed further below, in a preferred aspect of the present invention, manipulator 42 is formed in a manner and/or from a material or materials that accommodate a greater relative degree of flexibility of manipulator 42 than tube 30.

Still referring to FIG. 1, a tip 56 is secured and/or formed at an in vivo or subject facing end 46 of manipulator 42 and an opposing in vitro facing end 48 of manipulator 42 is secured to an in vivo or subject facing end 58 of connector 36 such that manipulator 42 extends in in vivo facing direction 44 relative to connector 36 and tube 30. In a preferred aspect, when in an at rest configuration, manipulator 42 extends along axis 50 but is formed of flexible material such that manipulator 42 is translatable relative to axis 50 in accordance with the disclosure provided below. In a preferred embodiment, axis 50 is disposed within a field of view 61, indicated by lines 60, 62, and that is generally defined by a conically shaped image capture area defined by image capturing device 40.

Preferably, field of view 61 has a generally conical shape although other shapes are envisioned and available as a function of the operation and construction of image capturing device 40. Further, although manipulator 42 is preferably captured within field of view 61 of image capturing device 40 throughout the entire range of motion available during deflection of manipulator 42 in the manner disclosed further below. It is however appreciated that other configurations and/or constructions of manipulator 42 are envisioned wherein tip 56 can be disposed outside field of view 61 and/or proximate thereto whether at rest or in a deflected configuration relative to connector 36 as disclosed further below.

Still referring to FIG. 1, one or more tethers or elongate operators 68, 70 cooperate with tip 56 and pass internally through each of the elongate body of manipulator 42, connector 36, tube 30, and a coupler or collar 74 that is constructed to removeably secure stylet assembly 20 to handle assembly 22. Operators 68, 70 are preferably formed of metal material such as solid or stranded wire or stainless steel and operable to effectuate communications of forces, such as compression, tension, or torsional forces from handle assembly 22 to tip 56 of stylet assembly to effectuate positional manipulation of manipulator 42 relative to connector 36. As disclosed further below, such operation allows the user to manipulate the relative shape or position of manipulator 42 from in vitro locations and allows the user to guide axial translation of stylet assembly 20 relative to the anatomy of the user and/or manipulate the relative position of anatomical features or structures within the field of view associated with operation of image capturing device 40.

An elongate communication tether 72 is operatively connected to imaging device 40, and any extraneous illumination device(s) when provided, and extends through connector 36 and tube 30 and is also operatively connected to handle assembly 22 or otherwise passes from stylet assembly 20 and passes in an in vitro direction to accommodate or otherwise facilitate the recording, capture, and/or display of information or images acquired by the image acquisition device 40 associated with connector 36. In a preferred embodiment, tether 72 is configured to communicate the information associated with operation of image capturing device 40 to locations external to the subject. It is appreciated that tether 72 could be configured as an electric signal communication tether, a fiber optic communication tether, or configured to provide another connection methodology associated therewith.

Regardless of the communication protocol employed, tether 72 and operators 68, 70 are configured to communicate the image acquisition information and the operational instructions associated with the relative configuration of manipulator 42 between the in vivo directed portion of stylet assembly 20 to in vitro direction portions or locations and preferable to handle assembly 22. Collar 74 is preferably configured to accommodate manual removeable connectivity of stylet assembly 20 with handle assembly 22 and is operationally connected to handle assembly 22 to facilitate manipulation or movement of manipulator 42 via operators 68, 70, and connectivity of tether 72 associated with operation of image capture device 40 with display devices disposed outside the subject during operation thereof.

Handle assembly 22 includes an input, such as a trigger 80 or the like, that is constructed to impart axial and/or rotational forces to operators 68, 70. As disclosed further below, forces imparted to operators 68, 70 are communicated to stylet assembly 20 and operative to effectuate changes in the relative orientation of manipulator 42 relative tube 30 and/or the position of tip 56 relative to connector 36. Preferably, operators 68, 70 extend in an uninterrupted manner through tube 30, connector 36, and the elongate body of manipulator 42 and are secured or otherwise connected or engaged with tip 56. Tether 72 associated with operation of image capturing device 40 is electronically connected to a display 82 or the like associated with providing the user a visually inspectable presentation of the image acquired thereby. Although shown as adjustably connected to handle assembly 22, it is appreciated that display 82 could be supported at other locations and/or otherwise remote from handle assembly 22.

Still referring to FIG. 1, it is appreciated that handle assembly 22 and stylet assembly 20 associated therewith, and the electronic components thereof, may be powered by external grid power sources and/or a replaceable or rechargeable power source 84 such as a battery or the like. Handle assembly 22 may further include one or more inputs 86, 88, 90, 92, 94 that are connected to control software or an integrated circuit board or control panel 96 or the like to facilitate the desired communication and operation of input signals received from inputs 86 through 94 to effectuate manipulation of the operation of image acquiring device 40 and/or any lights associated with operation thereof, and/or to manipulate the relative focus associated with operation thereof, the brightness or contrast associated with operation of display 82 so as to acquire a desired in vivo image contrast and presentation associated with use of stylet assembly 20 and operation of the imaging functions thereof.

The forthcoming disclosure directed to FIGS. 2-13 shows various views of each of tube 30, connector 36, manipulator 42, and tip 56 exploded from one another and with the respective structures of image acquisition device 40, operators 68, 70, and tether 72 removed therefrom. It should be understood that, when manufactured and/or assembled, tube 30, connector 36, manipulator 42, tip 46, operators 68, 70, image acquiring device 40, and tether 72 are rendered inseparable from one another without destruction of stylet assembly 20.

Figure 2:
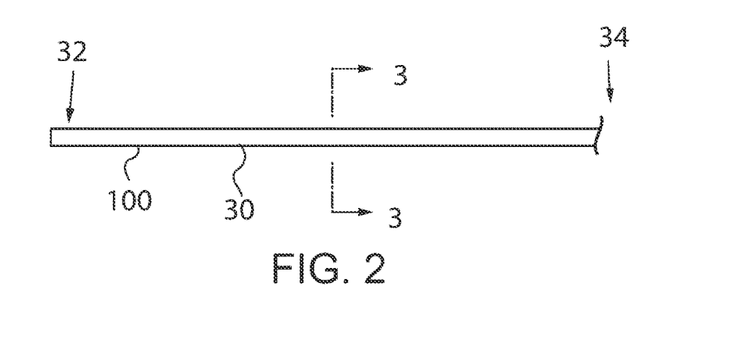
FIG. 2 is longitudinal side elevation view of an elongate tube of the stylet assembly shown in FIG. 1.
Figure 3:
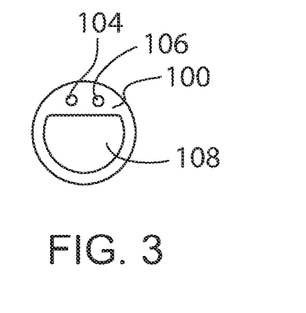
FIG. 3 is a radial cross section view of the elongate tube shown in FIG. 2 taken along line 3-3.
Figure 4:
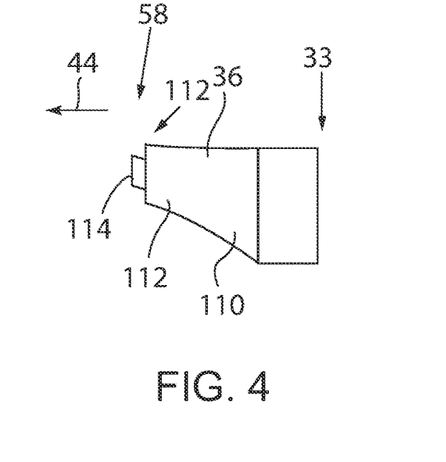
FIG. 4 is a radial side elevation view of a connector configured to engage the in vivo facing end of the tube shown in FIG. 2 of the stylet assembly shown in FIG. 1.

Referring to FIGS. 2 and 3, tube 30 is defined by an elongate body 100 that extends between in vivo facing end 32 and in vitro facing end 34. End 34 may be constructed to removeably cooperate with collar 74 (FIG. 1) or formed integrally therewith. Preferably, some degree of adjustability is provided at the interface of tube 30 and collar 74, such as via a ball and socket connection or the like, so as to allow variable positioning of stylet assembly 20 relative to handle assembly 22 to improve the ergonomics associated with use of the same.

Body 100 of tube 30 is preferably formed via an extrusion process and from materials such as medical grade PVC and/or nylon materials. Tube 30 is constructed to be somewhat flexible but is constructed in size, shape, and of materials that provide a degree of rigidity to tube 30 the facilitate the longitudinal translation of assembly 20 relative to an underlying subject without an unacceptable degree of deflection associated with the same and without compression thereof although tube 30 is preferably provided with sufficient flexibility to accommodate in vivo introduction of the same without unduly pressuring or otherwise irritating the structures and anatomy associated with introduction of the stylet assembly.

Referring to FIG. 3, body 100 of tube 30 defines a first passage 102 that extends longitudinally therethrough and a pair of passages 104, 106 that are fluidly isolated from passage 102. Passage 102 is constructed to accommodate passage of tether 72 therethrough whereas passages 104, 106 are constructed to accommodate passage of operators 68, 70 therethrough. Such a construction mitigates interference between tether 72 and operators 68, 70 and allows for the movable but supported association of operators 68, 70 with body 100 of tube 30.

FIGS. 4-7 are various views of connector 36. Connector 36 is defined by a body 110 that is preferably formed via a molding process and is formed of generally more rigid materials than tube 30 and/or manipulator 42, such as ABS or poly carbonate medical grade plastic materials suitable for molding processes. In vivo facing end 58 of connector 36 includes a conically shaped portion 112 that extends in vivo facing direction 44 and a projection 114 formed at a distal end thereof. In vitro facing end 33 of connector 36 is shaped to be permanently affixed to in vivo facing end 32 of tube 30 and so as to be inseparable therefrom. Body 110 of connector 36 also defines cavity 116 that is shaped to receive image acquiring device 40 (FIG. 1) in a secure and hermetically sealed manner. When employed, image acquiring device 40 may include an illumination means and/or body 110 may be shaped to accommodate extraneous light sources. When deployed in such a manner, it is appreciated that tether 72 may be configured to communicate the operational power to such illumination appliances.

Figure 5:
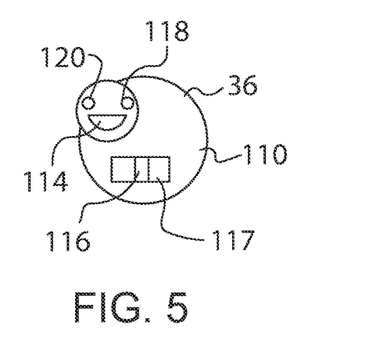
FIG. 5 is an elevation view of an in vivo facing end of the connector shown in FIG. 4.
Figure 6:
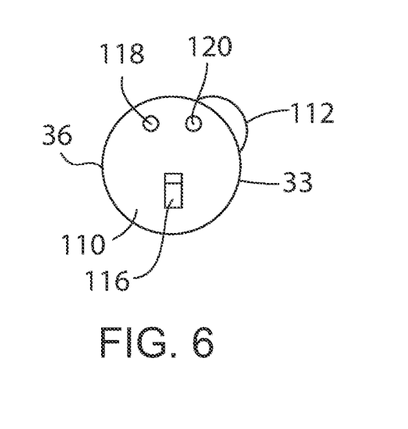
FIG. 6 is an elevation view of a tube facing end of the connector shown in FIG. 4.
Figure 7:
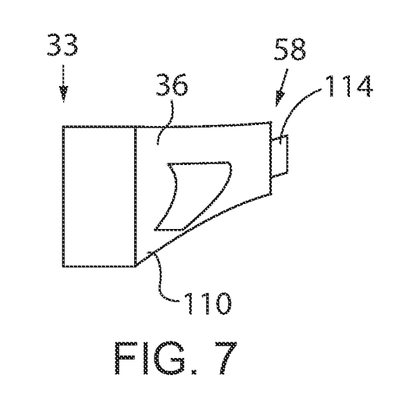
FIG. 7 is an elevation side view of the connector shown in FIG. 4 opposite the elevation side view shown therein.

In vivo facing end 58 of conical portion 112 includes a cutout 117 that generally flanks cavity 116 and is shaped to receive a lens or the like or to be molded with a transparent plastic material associated with maintaining the operational integrity of image acquiring device 40. As shown in FIGS. 5 and 6, it should be appreciated that conical portion 112 of connector 36 is non-centrically oriented relative to the longitudinal axis of body 110 and is shaped such that manipulator 42, when secured thereto as disclosed further below, progresses in a radially outward relative direction as manipulator 42 extends in in vivo facing direction 44 away from connector 36.

The first passage 118 and the second passage 120 formed through body 110 extend in an uninterrupted manner from in vitro facing end 33 to in vivo facing end 58 of body 110. Passages 118, 120 associated with in vitro facing end 33 of connector 36 are oriented to be generally aligned with passages 104, 106 defined by tube 30 such that passages 118, 120 accommodate the uninterrupted communication of operators 68, 70 through body 110 of connector 36.

Figure 8:
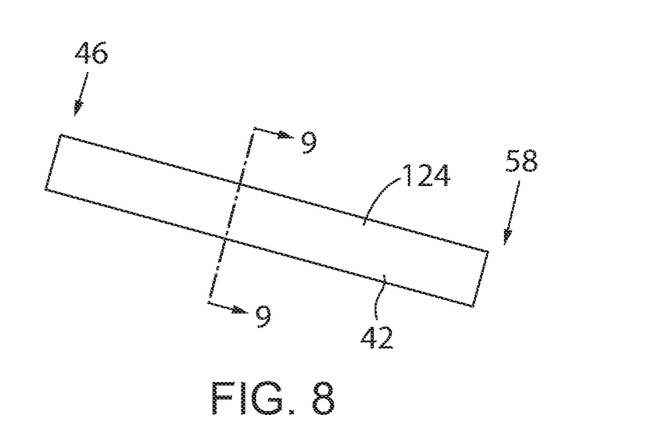
FIG. 8 is a side elevation view of a guide tube of the stylet assembly shown in FIG. 1.
Figure 9:
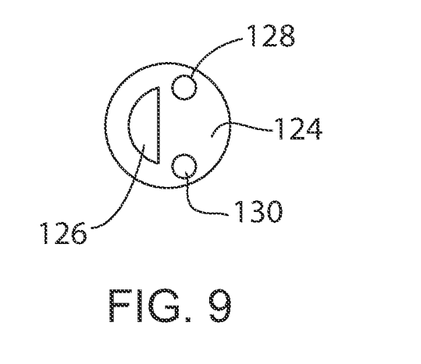
FIG. 9 is a radial cross section view of the guide tube shown in FIG. 8 taken along line 9-9.
Figure 10:
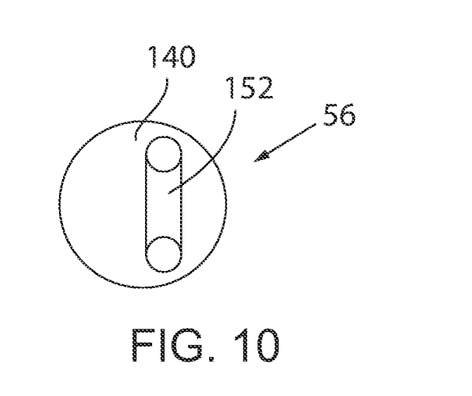
FIG. 10 is a plan view of an in vivo facing end of a guide tip of the stylet assembly shown in FIG. 1.
Figures 11, 12, 13:
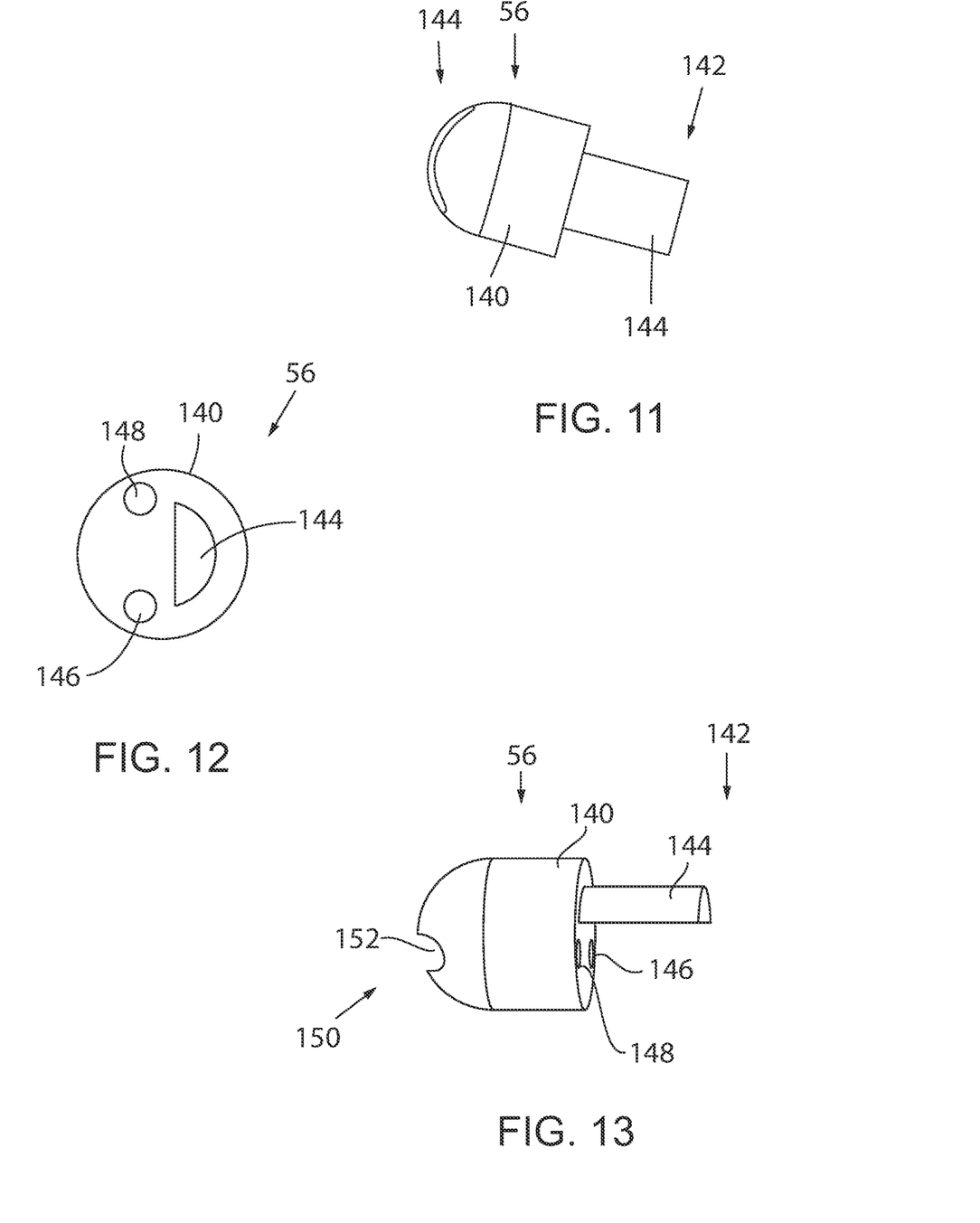
FIG. 11 is a side elevation view of the guide tip shown in FIG. 10.
FIG. 12 is an elevation view of a guide tube facing end of the guide tip shown in FIG. 10 and constructed to be secured to an in vivo facing end of the guide tube shown in FIG. 8.
FIG. 13 is a lateral side perspective view of the guide tip shown in FIG. 10.

As shown in FIGS. 8-10, manipulator 42 is defined by a body 124 that extends from the in vitro facing or connector facing end 58 to in vivo facing or distal end 46 of manipulator 42. As shown in FIGS. 9 and 10, body 124 of manipulator 42 defines a first cavity or passage 126 having a cross-sectional shape that is the same as projection 114 defined by connector 36. Additional passages 128, 130 extend through body 124 of manipulator 42 between connector facing end 58 and in vivo facing end 46 thereof.

Passages 128, 130 like passages 104, 106 of tube 30 and passages 118, 120 of connector 36 are shaped to accommodate the non-interrupted passage of operators 68, 70 through body 124 of manipulator 42 and in a manner that maintains isolation of operators 68, 70 from exposure to the environment associated with use of stylet assembly 20. As mentioned above, body 124 of manipulator 42 is preferably formed via an extrusion process from a PVC or nylon type medical grade material such that the same is constructed to provide sufficient axial resistance to compression yet flexible enough to accommodate deflection, displacement, or translation of manipulator 42 relative to connector 36 and to accommodate flexure thereof in response to mechanical input signals, such as compression, tension, or torsional forces, communicated thereto via operators 68, 70. That is, as disclosed further below, axial or rotational translation of either of operators 68, 70 communicated from handle assembly 22 to distal ends 26 of stylet assembly 20 allows manipulator 42 to be displaced from the at rest configuration, as shown in FIG. 1, to configurations wherein manipulator 42 can be bent in any radial direction relative to the at rest linear axial shape of manipulator 42 when otherwise not acted upon via forces imparted via operators 68, 70.

Referring to FIGS. 10-13, tip 56 associated with distal in vivo facing end 26 of stylet assembly 20 is defined by a body 140 that extends between an in vitro or manipulator facing end 43 and an in vivo facing or terminal end thereof 144. Body 140 includes a projection 144 proximate manipulator facing end 142. Projection 144 is constructed to slideably cooperate with passage 126 defined by body 124 of manipulator 42 when secured thereto. The respective cooperation of discrete projections 114 and 144 of connector 36 and tip 56 ensure the desired relative rotational orientation of tip 56 relative to manipulator 42 and manipulator 42 relative to connector 36 to provide the desired rotational alignment of respective passages 104, 106, 118, 120, 128, 130, 146, 148 during assembly of stylet assembly 20 to accommodate the slideable association of the discrete operators 68, 70 therewith.

Still referring to FIGS. 10-13, body 140 of tip 56 defines a first passage 146 and a second passage 148 that are each constructed to cooperate with a respective one of operators 68, 70. Forward facing surface 150 of body 140 includes a cutout 152 that is shaped to facilitate guided interaction with a body defined by the continuous continuity associated with operators 68, 70. When fully assembled, cutout 152 is configured to be populated with an insert of the like such that the in vivo facing end 26 of stylus assembly 20 has a generally continuous curved contour. Tip 56 is preferably constructed via a molding methodology and is preferably constructed of ABS or poly carbonate type medical grade plastic materials. Population of cutout 152 with an insert or the like secures the relative position of a respective "terminal end" of each of operators 68, 70 relative to tip 56. As mentioned above, although secured threat, it is appreciated that operators 68, 70 are preferably provided in a continuous manner between handle assembly 22 and tip 56 such that the continuity associated with operators 68, 70 is positionally fixed relative to tip 56 but in that each of the respective portions that extend in the in vitro direction rearward therefrom are discreetly independently rotatable and/or compressible and/or retractable relative to manipulator 42, connector 36 and tube 30.

During use of stylet assembly 20, communication of a compressive, tensile, or rotational force via either or both of operators 68, 70 allows user interaction with handle assembly 22 to effectuate the translation and/or other positional manipulation of tip 56 of stylet assembly 20 relative to connector 36 and tube 30 via the bending or twisting of manipulator 42. Allowing such deflection and/or manipulation of tip 56 is preferably within the field of view 61 associated with image acquiring device 40, such manipulation allows operation of stylet assembly 20 in a manner wherein manipulator 42 can be employed to improve the longitudinal guided insertion of stylet assembly 20 relative to an underlying subject and/or to manipulate anatomy and/or other structures or features associated with impeding such insertion and or obstructing the desired field of view or visual acquisition associated with operation of image acquiring device 40. Accordingly, stylet assembly 20 allows users thereof greater freedom associated with the introduction of the stylet assembly to the underlying subject as well as the manipulation of adjacent anatomy and/or structures that may otherwise hinder access or inspection of areas of intended observation. Positioning tip 56 in the in vivo direction forward of imaging acquiring device 40 provides the user with the capability to manipulate in vivo structures and in a manner that facilitates visual inspection of the manipulation operation as well as the areas of intended interest.

Therefore, one embodiment of the application includes a stylet assembly and method of forming an in vivo image acquiring stylet assembly having an elongate flexible body and an image acquiring device that is supported at a location that is offset from a terminal end of the stylet assembly. A terminal end portion of the stylet assembly is defined by a manipulator that is oriented to extend in a crossing direction relative to a longitudinal axis of the elongate body. The terminal end portion of the stylet assembly is steerable relative to the elongate body and is operable to manipulate positions or adjacent anatomy and/or effectuate guidance of the imaging device relative thereto during use.

Another embodiment of the application that is useable or combinable with one or more of the features, aspects, or objects of the above embodiment discloses a stylet assembly having a tube that defines a passage therethrough. An image acquisition device, such as a camera, lens, or the like, is disposed proximate a first end of the tube. A connector is formed at the first end of the tube and is constructed such that the camera is operable therethrough. A manipulator that is defined by a flexible body extends outward from the connector and is oriented to extend in a crossing direction relative to a longitudinal axis of the tube such that a distal end of the manipulator forms a distal end of the stylet assembly. The manipulator is offset in a longitudinal and radial direction from the camera and is offset from a longitudinal axis of the tube such that a distal end of the manipulator is disposed deeper or further in vivo than the image acquisition device such that operation of the manipulator is capable of visual inspection by the image acquisition device.

Yet another embodiment of the present invention that is useable or combinable with one or more of the features, aspects, or features of the above embodiments includes a video stylet assembly having an elongate shaft that is constructed to pass through an opening in vivo. A connector is disposed proximate an in vivo end of the elongate shaft and an image capturing device is disposed proximate the connector. A guide extends in a longitudinal manner from the connector in a crossing direction relative to a longitudinal axis defined by the elongate shaft. The guide is oriented relative to the connector and the image capturing device such that a distal end of the guide can achieve positions within a field of view of the image capturing device during movement thereof.

Yet another embodiment of the present invention that is useable or combinable with one or more of the various features, aspects, or features of the above embodiments includes a method of forming an imaging stylet that includes providing a flexible outer housing having a patient facing end that is configured to pass in an in vivo direction. A connector is formed at the patient facing end of the housing and is inseparable therefrom. The method further includes forming the connector to receive an image acquisition device such that the image acquisition device is disposed proximate the patient facing end of the flexible outer housing. The method includes forming a manipulator that extends further in the in vivo direction than the connector and is formed to be deflectable relative to the connector such that a distal end of the manipulator is disposed further in vivo than the image acquisition device and is operable to manipulate the orientation or position of anatomy or features relative thereto and in a manner that is preferably within a field of view of the image acquisition device.

It is also understood that, although the foregoing description and drawings describe and illustrate in detail the preferred aspects of the present invention, to those skilled in the art to which the present invention relates, the present disclosure will suggest many modifications and constructions as well as widely differing embodiments and applications without departing from the sprit and scope of the invention. The present invention, therefore, is intended to be limited only by the scope the applicable prior art.

Further, the invention may be implemented in a variety of configurations, using certain features or aspects described herein and others known in the art. Thus, although the invention has been shown and described in what is perceived to be the most practical and preferred embodiments, it is to be understood that the invention is not intended to be limited to the specific features set forth above. Rather, it is recognized that modifications may be made by those skilled in the art of the invention without departing from the spirit or intent of the invention and, therefore, the invention is to be taken as including all reasonable equivalents to the subject matter of the claims.

What is claimed is:

1. A stylet assembly comprising:
a tube having a passage formed therethrough;
a camera disposed proximate a first end of the tube;
a connector formed at the first end of the tube and constructed such that the camera is supported by and operable therethrough, the connector defining an in vitro facing end constructed to be secured to the tube and an in vivo facing end formed by a conical portion that is non-centrically oriented relative to a longitudinal axis of the connector; and
a manipulator defined by a flexible body that extends outward from the connector and constructed to be secured to an in vivo facing end of the conical portion of the connector and oriented to extend in a crossing direction relative to a longitudinal axis of the tube such that a distal end of the manipulator forms a distal end of the stylet assembly, is offset in a longitudinal and radial direction from the camera, and is offset from a longitudinal axis of the tube.

2. The stylet assembly of claim 1 further comprising at least one elongate operator that passes through the tube and is operable to manipulate a position of the distal end of the manipulator relative to the connector in response to manipulation of the at least one elongate operator.

3. The stylet assembly of claim 2 wherein the at least one elongate operator is further defined as two independently operable elongate operators.

4. The stylet assembly of claim 2 wherein the at least one elongate operator is at least one of longitudinally translatable and rotationally translatable relative to the tube to manipulate a relative position of the distal end of the stylet assembly.

5. The stylet assembly of claim 2 further comprising an elongate tether that passes through the tube and is operatively connected to the camera.

6. The stylet assembly of claim 1 wherein the distal end of the stylet assembly is within a field of view of the camera.

7. The stylet assembly of claim 1 further comprising a lens supported by the connector and disposed proximate the camera.

8. The stylet assembly of claim 1 where the tube is formed of a first material and the manipulator is formed of a second material having a lower durometer than the first material.

9. A video stylet assembly comprising:
an elongate shaft constructed to pass through an opening in vivo;
a connector disposed proximate an in vivo end of the elongate shaft and having a conical portion that extends in an in vivo facing direction and has a projection formed at an in vivo end thereof having a smaller cross sectional shape than a cross sectional shape of the elongate shaft;
an image capturing device disposed proximate the connector; and
a guide secured to the projection of at the in vivo facing end of the conical portion of the connector and extending longitudinally from the connector in a crossing direction relative to a longitudinal axis defined by the elongate shaft and oriented such that a distal end of the guide can achieve positions within a field of view of the image capturing device.

10. The video stylet assembly of claim 9 further comprising a light source associated with the image capturing device and operable to illuminate the field of view of the image capturing device.

11. The video stylet assembly of claim 9 further comprising at least one operator extending through the elongate shaft and operable to manipulate an orientation of the guide relative to the elongate shaft.

12. The video stylet assembly of claim 11 wherein the at least one operator is at least one of rotationally and longitudinally translatable relative to the elongate shaft to manipulate the orientation of the guide relative to the elongate shaft.

13. The video stylet assembly of claim 12 further comprising a controller connected to the video stylet assembly and having at least one input connected to the at least one operator, the controller being operable to allow user adjustment of the at least one operator.

14. The video stylet assembly of claim 9 further comprising an image generating device operatively connected to the image capturing device.

15. The video system assembly of claim 9 wherein the elongate shaft is more rigid than the guide.

16. The video system assembly of claim 9 further comprising a lens supported by the connector and disposed proximate the imaging capturing device.

* * * * *